(12) United States Patent
Cai et al.

(10) Patent No.: US 10,562,889 B2
(45) Date of Patent: Feb. 18, 2020

(54) PROCESS FOR THE PREPARATION OF 1-(ARYLMETHYL)QUINAZOLINE-2,4 (1H,3H)-DIONES

(71) Applicant: IMPACT THERAPEUTICS, INC., Shanghai (CN)

(72) Inventors: Suixiong Cai, Shanghai (CN); Ping Huang, Shanghai (CN)

(73) Assignee: IMPACT THERAPEUTICS, INC., Shanghai (CN)

( * ) Notice: Subject to any disclaimer, the term of this patent is extended or adjusted under 35 U.S.C. 154(b) by 0 days.

(21) Appl. No.: 16/089,486

(22) PCT Filed: Mar. 31, 2017

(86) PCT No.: PCT/CN2017/078913
§ 371 (c)(1),
(2) Date: Sep. 28, 2018

(87) PCT Pub. No.: WO2017/167251
PCT Pub. Date: Oct. 5, 2017

(65) Prior Publication Data
US 2019/0112298 A1    Apr. 18, 2019

(30) Foreign Application Priority Data

Apr. 1, 2016 (CN) .......................... 2016 1 0202881

(51) Int. Cl.
*C07D 403/14* (2006.01)
*C07D 239/96* (2006.01)
*B01D 9/00* (2006.01)

(52) U.S. Cl.
CPC ......... *C07D 403/14* (2013.01); *C07D 239/96* (2013.01); *B01D 9/005* (2013.01)

(58) Field of Classification Search
CPC ......................... C07D 403/14; C07D 239/96
USPC ....................................................... 544/284
See application file for complete search history.

(56) References Cited

U.S. PATENT DOCUMENTS

| | | | | |
|---|---|---|---|---|
| 9,290,460 B2* | 3/2016 | Cai | .................. | C07D 239/96 |
| 9,926,304 B2* | 3/2018 | Cai | .................. | C07D 239/96 |
| 2012/0065216 A1* | 3/2012 | Kennis | ................. | C07D 401/04 |
| | | | | 514/266.22 |
| 2014/0023642 A1* | 1/2014 | Cai | .................. | C07D 239/96 |
| | | | | 424/133.1 |
| 2014/0031358 A1* | 1/2014 | Liu | .................. | C07D 239/80 |
| | | | | 514/249 |
| 2014/0275711 A1* | 9/2014 | Cai | .................. | C07D 239/90 |
| | | | | 600/1 |
| 2016/0237070 A1* | 8/2016 | Cai | .................. | C07D 239/96 |
| 2018/0071290 A1* | 3/2018 | Cai | .................. | A61K 47/32 |
| 2018/0215741 A1* | 8/2018 | Cai | .................. | C07D 239/96 |

FOREIGN PATENT DOCUMENTS

| | | | | |
|---|---|---|---|---|
| CN | 103097361 B | 5/2013 | | |
| WO | WO-2012125521 A1 * | 9/2012 | ........... | C07D 239/80 |
| WO | WO 2012/130166 A1 | 10/2012 | | |
| WO | WO-2017109722 A1 * | 6/2017 | ............ | C07F 9/5728 |

OTHER PUBLICATIONS

Basavaprabhu; Synthesis 2013, 45, 1569-1601. DOI: 10.1055/s-0033-1338989 (Year: 2013).*
European Patent Office; Search Opinion and Supplementary Search Report, Application EP17773281, 5 pages, dated Jul. 23, 2019. (Year: 2019).*
International Search Report for International Application No. PCT/CN2017/078913, State Intellectual Property Office of the P.R. China, Beijing, China, dated Jun. 29, 2017, 2 pages.

\* cited by examiner

*Primary Examiner* — Daniel R Carcanague
(74) *Attorney, Agent, or Firm* — Sterne, Kessler, Goldstein & Fox P.L.L.C.

(57) ABSTRACT

This disclosure provides a process for preparing 1-(arylmethyl)quinazoline-2,4(1H,3H)-diones, specially provides a method for preparing the compound of Formula I, and the method comprises the step of reacting the compound of Formula II with the compound of Formula A in the presence of a condensation agent, an organic base and an organic solvent by condensation.

20 Claims, No Drawings

PROCESS FOR THE PREPARATION OF 1-(ARYLMETHYL)QUINAZOLINE-2,4(1H,3H)-DIONES

FIELD OF THE INVENTION

This disclosure discloses an improved process for synthesizing (arylmethyl)quinazoline-2,4(1H,3)-diones, such as 5-fluoro-1-(4-fluoro-3-(4-(pyrimidin-2-yl)piperazine-1-carbonyl)benzyl)quinazoline-2,4(1H,3H)-dione, which is a potent poly(ADP-ribose)polymerase (PARP) inhibitor.

RELATED ART

Poly (ADP-ribose) polymerase (PARP) catalyzes the addition of poly (ADP-ribose) to the target protein using NAD+, which is an important process in DNA, repair. This is an essential process for maintaining the integrity and stability of DNA and chromosome, and for ensuring the survival of mammalian cells. PARP-1 catalyzes the majority of the intracellular ADP-ribose polymerization reactions, although PARP-2 and other subtypes also have this function. The PARP-1 knockout mice do not have the repair function for single-stranded DNA damages (Krishnakumar R and Kraus W L. Mol Cell, 2010, 39(1): 8-24). Cancer cells with DNA repair defects, such as BRCA1 (breast cancer 1) or BRCA2 (breast cancer 2) deficient cancer cells, are particularly sensitive to DNA damaging anticancer agents, including platinum chemotherapy drugs, DNA methylation anti-cancer drugs and DNA topoisomerase inhibitors, or radiation therapy. There are multiple PARP inhibitors in clinical at present, wherein Olaparib (Lynparza, AZD2281) was approved by EMEA and FDA for the maintenance and treatment of BRCA mutated advanced ovarian cancer in December 2014. These scientific and clinical results demonstrated that PARP inhibitors may be used as effective anti-cancer drugs to treat a variety of cancers. The applications of PARP inhibitors for the treatment of cancer are mainly based on two mechanisms. First, because of the rapid growth, DNA replication is much higher in cancer cells than in normal cells. Drugs that cause DNA damage will induce cancer cell death selectively. However, due to the presence of DNA repair enzymes such as PARP, the therapeutic effects of these drugs can not be fully materialized. By inhibiting the DNA repair mechanism, PARP inhibitors in combination with commonly used DNA damaging anti-cancer drugs, such as temozolomide, can achieve synergy effects and greatly enhance the anticancer effects of currently used DNA damaging anticancer drugs. Second, for cancer cells with DNA repair deficiency, such as BRCA1 or BRCA2 deficient triple-negative breast cancer cells, PARP inhibitors can directly kill the cancer cells and function as anticancer drugs independently.

Syntheses of 1-(arylmethyl)quinazoline-2,4(1H,3H)-diones as PARP inhibitors are disclosed in WO2012130166A1, the content of which is hereby incorporated by reference in its entirety. However, the synthetic routes disclosed in WO2012130166A1 present scale-up challenges, including the preparation of 5-fluoro-1-(4-fluoro-3-(4-(pyrimidin-2-yl)piperazine-1-carbonyl)benzyl) quinazoline-2,4(1H,3H)-dione. Accordingly, there exists a need to provide alternative or improved methods for their preparation, particularly for large scale and environmentally-friendly manufacturing.

SUMMARY OF THE DISCLOSURE

The present disclosure provides an improved process for synthesizing 5-fluoro-1-(4-fluoro-3-(4-(pyrimidin-2-yl)piperazine-1-carbonyl)benzyl)quinazoline-2,4(1H,3H)-dione as represented by Formula I.

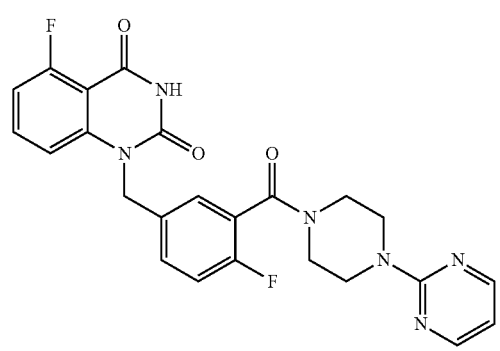

In particular, the total yield of four-step reaction for preparing 5-fluoro-1-(4-fluoro-3-(4-(pyrimidin-2-yl)piperazine-1-carbonyl)benzyl)quinazoline-2,4(1H,3H)-dione (Formula I) in the present disclosure is relatively high, which is 55.6%. Column chromatography separation and purification is not needed during the whole synthetic process, and thus the present process is particularly suitable for large-scale industrial production. Compared with the existing technology, such as Example 132 disclosed in WO2012130166A1 (see Examples 1, 2, 3 and 76), methods of the present disclosure has great advantages in terms of synthetic process and yield.

Specifically, a compound of Formula I is prepared by a method comprising the following step:

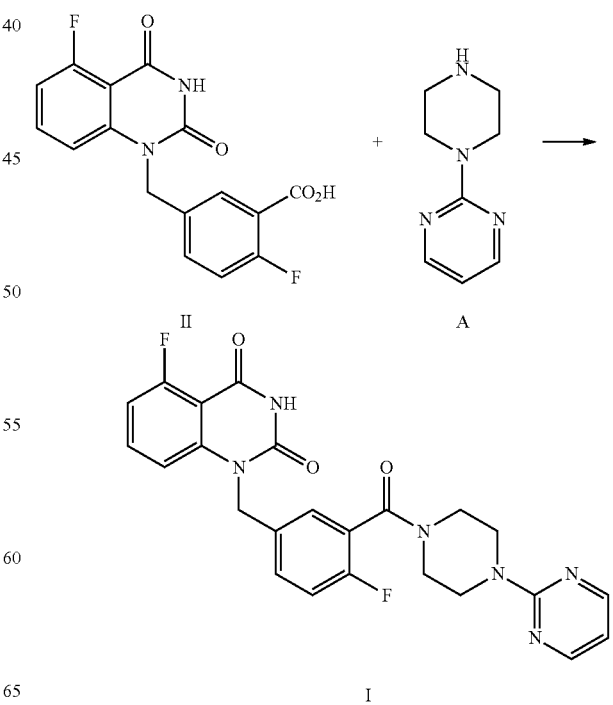

reacting a compound of Formula II with a compound of Formula A in the presence of a condensation agent, an organic base and an organic solvent by condensation.

In one or more embodiments, the condensation agent is selected from HATU (1-(bis(dimethylamino)methylene)-1H-1,2,3-triazolo[4,5-b]pyridinium 3-oxidhexafluorophosphate), TBTU (O-(benzotriazol-1-yl)-N,N,N',N'-tetramethyronium tetrafluoroborate), HBTU (O-benzotriazole-N,N,N',N'-tetramethyl-uronium-hexafluorophosphate), and $T_3P$ (propyl phosphoric acid anhydride), or any mixture thereof.

In one or more embodiments, the condensation agent is $T_3P$.

In one or more embodiments, for 1 mol of the compound of Formula II, 1.3~2.0 mol of the condensation agent is used.

In one or more embodiments, the organic base is selected from NMM (N-methylmorpholine) and DIPEA (N,N-di(isopropyl)ethylamine), or any mixture thereof.

In one or more embodiments, the organic base is DIPEA.

In one or more embodiments, or 1 mol of the compound of Formula II, 2.8~3.5 mol of the organic base is used, especially DIPEA.

In one or more embodiments, the organic solvent is EtOAc.

In one or more embodiments, the volume ratio of the organic solvent to the compound of Formula II is 15~30, preferably 15~25.

In one or more embodiments, a mixture of the compound of Formula II, an organic solvent, a condensation agent and an organic base is stirred at 65~75° C. until all solids are dissolved completely, and then the compound A is added.

In one or more embodiments, the solvent is EtOAc; the condensation agent is $T_3P$; the organic base is DIPEA; the mixture is stirred at 65~75° C. for 10~20 min.

In one or more embodiments, for 1 mol of the compound of Formula II, 1.0~1.3 mol of the compound A is used.

In one or more embodiments, a mixture of the compound of Formula II and the compound of Formula A is stirred at 70~80° C. to allow for a condensation reaction.

In one or more embodiments, the compound A is dissolved in the same organic solvent used to dissolve the compound of Formula II.

In one or more embodiments, the stirring time is 12~16 hours.

In one or more embodiments, after stirring at 70~80° C., the reaction liquid is cooled to 0~5° C., and stirred for another 4~6 hours, and then filtered to provide the compound of Formula I.

In one or more embodiments, after the reaction is finished and the filtration is completed, the solid obtained by filtration is slurried with an organic solvent at 0~5° C., and then filtered to provide the compound of Formula I.

In, one or more embodiments, the slurry time is 3~7 hours, preferably 4~6 hours.

In one or more embodiments, before slurry, the solid obtained by filtration is washed with an organic solvent.

In one or more embodiments, after slurry and filtration, the solid obtained by filtration is washed with an organic solvent again.

In one or more embodiments, the organic solvent used for slurry and, washing is EtOAc.

In one or more embodiments, the volume ratio of the organic solvent used for slurry to the compound of Formula II used for the initial reaction is 1~5, preferably 2~3.

In one or more embodiments, the said process also comprises recrystallization of the product I obtained by condensation reaction in a suitable solvent to provide a purified compound of Formula I.

In one or more embodiments, the solvents used for recrystallization are DMSO and water.

In one or more embodiments, the product I obtained by condensation reaction, is dissolved, in DMSO (the volume ratio of DMSO to the compound of Formula I is within 10), and the mixture is stirred at 15~25° C. for 2~4 hours, then pure water (the volume ratio of water to the compound of Formula I is within 10) is added dropwise within 2 hours. The mixture is stirred at 15~25° C. for 8~10 hours and then filtered; preferably, the filter cake is slurried with pure water (the volume ratio of pure water to the compound of Formula I is within 10) at the above temperature for 4~6 hours, and filtered; the filter cake is washed with pure water, and dried under vacuum to provide the purified compound of Formula I.

In one or more embodiments, a compound of Formula II is prepared by a method comprising the following step:

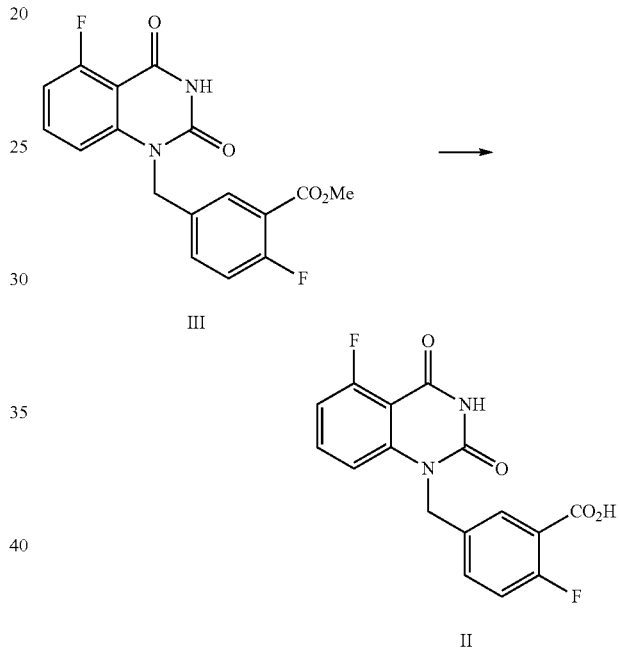

hydrolyzing the compound of Formula III in the presence of an inorganic base in a solvent, and then adjusting the pH value of the reaction liquor to 2~3 to provide the compound of Formula II.

In one or more embodiments, the solvent is selected from alcoholic solvent, such as MeOH and/or EtOH; and/or water.

In one or more embodiments, the volume ratio of the used solvent to the compound of Formula III is 0.8~1.3.

In one or more embodiments, the volume ratio of the used alcohols solvent to the compound of Formula III is 0.8~1.3.

In one, or more embodiments, the inorganic base is KOH and/or NaOH.

In one or more embodiments, for 1 mol of the compound of Formula III, 1.5~2.0 mol of the inorganic, base is used.

In one or more embodiments, an aqueous inorganic base solution is used, wherein the volume ratio of water in the aqueous inorganic base solution to the compound of Formula III is 2.8~3.5.

In one or more embodiments, a mixture of the compound of Formula III, an organic solvent and an aqueous inorganic base solution is stirred at 40~50° C. for 16~30 hours, preferably 24~30 hours, allowing for hydrolysis reaction.

In one or more embodiments, after the hydrolysis reaction is finished, the reaction liquid is cooled to 10~25° C., water (the volume ratio of water to the compound of Formula III is 5.0~9.0) is added and an inorganic acid is added dropwise to adjust the pH value of the reaction liquid to 2~3, and the mixture is stirred for 1~2 hours, and filtered to provide the compound of Formula II.

In one or more embodiments, a compound of Formula III is prepared by the method comprising the following steps:

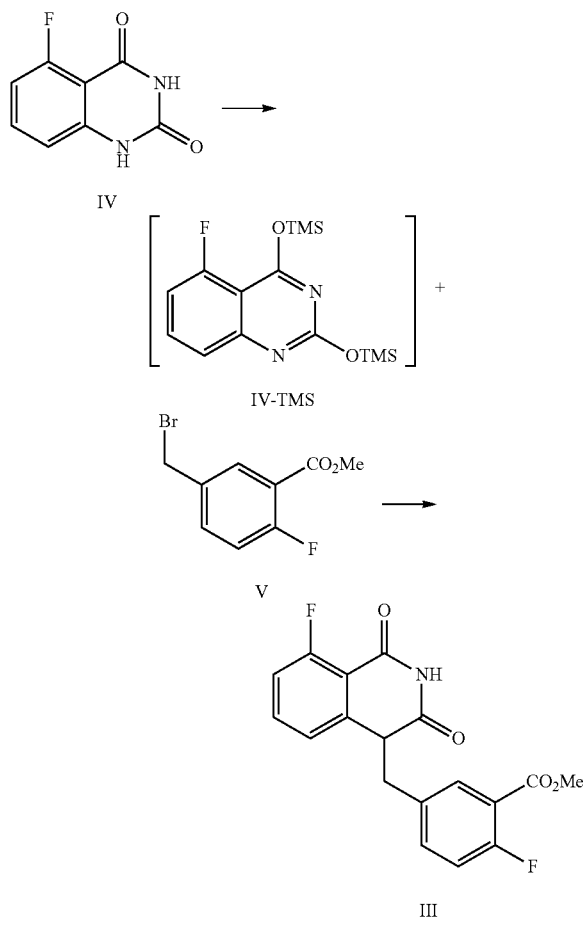

1) reflux reacting the compound of Formula IV with hexamethyldisilazane in the presence of an inorganic acid in an organic solvent to prepare the intermediate shown in Formula IV-TMS, which is protected by trimethylsiloxy group (TMS); and 2) under anhydrous condition, reflux reacting the intermediate of Formula IV-TMS with the compound of Formula V in an organic solvent to provide the compound of Formula III.

In one or more embodiments, the organic solvent used in step 1) is toluene.

In one or more embodiments, the inorganic acid used in step 1) is sulfuric acid.

In one or more embodiments, the volume ratio of the used solvent to the compound of Formula IV is 7~9.

In one or more embodiments, for 1 mol of the compound of Formula IV, 2.0~3.0 mol of hexamethyldisilazane is used.

In one or more embodiments, for 1 mol of the compound of Formula IV, 0.04~0.06 mol of the inorganic acid is used.

In one or more embodiments, refluxing in step 1) comprises stirring at 105~120° C. until all solids are dissolved completely.

In one or more embodiments, after refluxing, the reaction liquid is cooled to 55~65° C. in an inert atmosphere (such as nitrogen) and concentrated, then the obtained concentrated liquid is cooled to 15~30° C. in the inert atmosphere to provide the compound of Formula IV-TMS.

In one or more embodiments, the compound of Formula V in step 2) can be obtained from commercial sources or prepared using the methods known to one skilled in the art.

In one or more embodiments, the organic solvent in step 2) is NMP (N-methyl-2-pyrrolidone) and/or DMF (N,N-dimethylformamide).

In one or more embodiments, refluxing in step 2) comprises stirring at 105~115° C. for 12~18 hours.

In one or more embodiments, for 1 mol of the compound of Formula IV-TMS, 1.0~1.3 mol of the compound of Formula V is used.

In one or more embodiments, after refluxing in step 2) is finished, dioxane is added to the reaction liquid, and the reaction liquid is cooled to 65~75° C., and then an alcoholic solvent is added, and the mixture is stirred at 65~75° C. for additional 0.5~1 hours.

In one or more embodiments, the volume ratio of the used dioxane to the compound of Formula IV-TMS is 1.0~1.5.

In one or more embodiments, the alcoholic solvent is MeOH and/or EtOH, and the volume ratio of the alcoholic solvent to the compound of Formula IV-TMS is 2.5~3.5.

In one or more embodiments, the reaction liquid is stirred at 65~75° C. for another 0.5~1 hour, then, cooled to 0~5° C. and stirred for 1~2 hours, and filtered to provide the compound of Formula III.

In one or more embodiments, a compound of Formula IV is prepared by the method comprising the following steps:

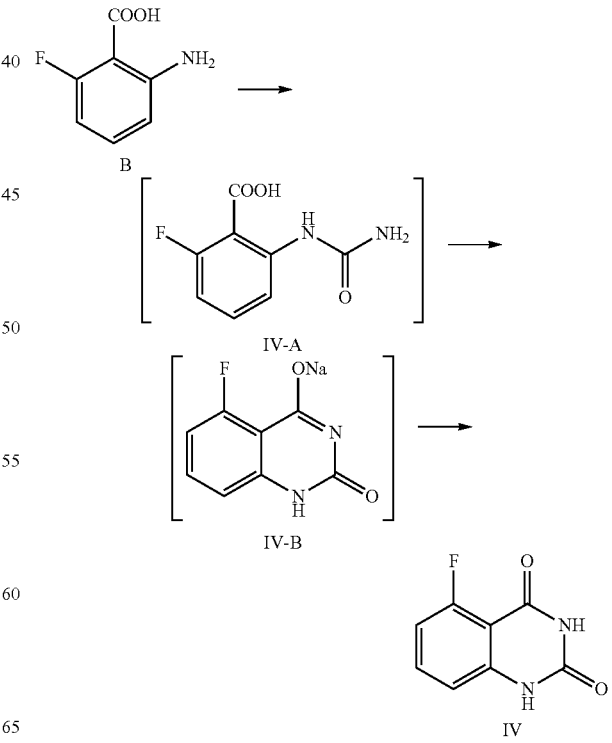

1) reacting the compound B with an aqueous cyanate solution, and then with an aqueous inorganic base solution; and 2) adjusting the pH value of the aqueous solution of the product in step 1) to 5~6 to provide the compound of Formula IV.

In one or more embodiments, cyanate is KOCN.

In one or more embodiments, for 1 mol of the compound of Formula B, 1.0~1.5 mol of cyanate is used, and the volume ratio of water in the aqueous cyanate solution to the compound of Formula B is 2.0~3.0.

In one or more embodiments, in step 1) the compound of Formula B is added to water, then acetic acid is added and the mixture is stirred at 5~15° C.

In one or more embodiments, the amount of water is 30~40 times volume of the compound of Formula B, and for 1 mol of the compound of Formula B, 1.0~1.5 mol of acetic acid is used.

In, one or more embodiments, the aqueous cyanate solution is added to a mixed liquid of the compound of Formula B, acetic acid and water dropwise at 5~15° C., and the mixture is stirred until the reaction is completed.

In one or more embodiments, the aqueous inorganic base solution is an aqueous solution of KOH and/or NaOH.

In one or more embodiments, the said aqueous inorganic base solution is prepared by dissolving the inorganic base in some water, wherein the amount of the inorganic base is 7.0~8.0 mol for 1 mol of the compound of Formula B, and the amount of water is 2~4 times volume of the compound of Formula B.

In one or more embodiments, the aqueous inorganic base solution is added dropwise below 0° C., and then the mixture is stirred at 10~25° C. until the reaction is completed.

In one or more embodiments, after stirring at 10~25° C. until the reaction is completed, the reaction liquid is cooled to 0~5° C., stirred for another 2~4 hours, and filtered.

In one, or more embodiments, step 2) comprises adding the product obtained from step 1) to water, increasing the temperature to 85~95° C., stirring the mixture for 1.5~3 hours to get the aqueous solution of the said reaction product.

In one or more embodiments, the product from step 1) is dissolved in a requited amount of water (the volume ratio of water to the compound of formula B is 25~35).

In one or more embodiments, the pH value of the reaction liquid is adjusted to 5~6 with acetic acid. After stirred at 85~95° C. for 1~3 hours, the reaction liquid is cooled to 0~5° C., stirred for 2~4 hours, and filtered to provide the compound of Formula IV.

The application also includes the methods for preparing the compounds of Formulae I, II, III and IV, which are as stated in each part respectively.

The application also includes the compounds of Formulae I, II, III and IV.

The application also includes the use of each compound of Formulae A, B, II, III and IV in preparing the compound of Formula I.

The application also includes the products of Formula II, III, or IV obtained from the above preparation steps, and includes but not limited to various kinds of solutions, filtrates, filter cakes and, so on.

DETAILED DESCRIPTION OF THE DISCLOSURE

The present disclosure provides an improved synthetic route and process for preparing 1-(arylmethyl)quinazoline-2,4(1H,3H)-diones, especially the compound of Formula I or pharmaceutically acceptable salts, hydrates or solvates thereof:

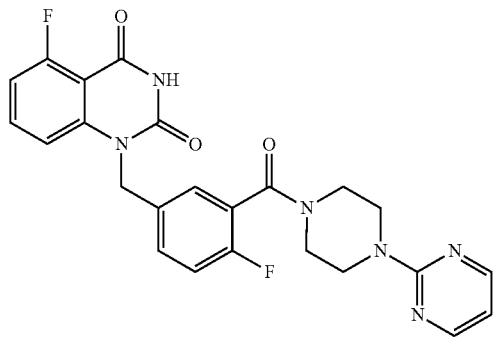

The process comprises the step of reacting the compound of Formula II with (pyrimidin-2-yl)piperazine A by condensation:

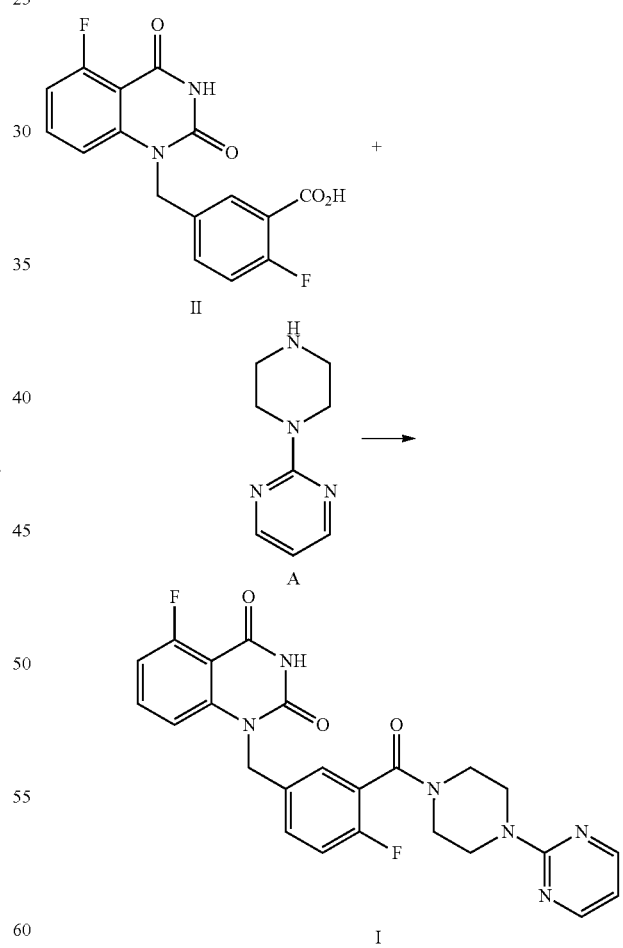

In one or more embodiments, firstly the compound of Formula II is dissolved in a suitable organic solvent (such as EtOAc), then a suitable condensation agent (such as HATU, TBTU, HBTU, T$_3$P and the like) and a suitable organic base (such as NMM, DIPEA, and the like) are added, and the reaction liquid is stirred at a suitable temperature (such as 65~75° C.) for a suitable period of time (such as 10~20 min).

In general, for 1 mol of the compound of Formula II, about 1.3~2.0 mol of the condensation agent and about 2.8~3.5 mol of the organic base are used; the amount of the organic solvent is usually 15~30 times volume of the used compound of Formula II, such as 15~25 times.

Preferably, the suitable solvent is EtOAc; the suitable condensation agent is T$_3$P; the suitable organic base is DIPEA; the reaction liquid is stirred at 65~75° C. for 10~20 mm.

Preferably, for 1 mol of the compound of Formula II, the suitable condensation agent is about 1.6 mol of T$_3$P; the suitable organic base is about 3.2 mol of DIPEA; the solvent is EtOAc, and the volume ratio of EtOAc to the compound of Formula II is about 20.

And then the compound A, (pyrimidin-2-yl)piperazine, is added at a suitable temperature (such as about 70~80° C., preferably 73~80° C.), and the reaction liquid is stirred at a suitable temperature (such as 70~80° C., such as about 75° C.) for a suitable period of time (such as about 12~16 hours). For 1 mol of the compound of Formula II, 1.0~1.3 mol of the compound A can be used. Preferably, the compound A is dissolved in the same solvent (such as EtOAc), used to dissolve the compound of Formula II in the previous step.

After the reaction is finished, the reaction liquid is cooled to a suitable temperature (such as about 0~5° C.), stirred at this temperature for a suitable period of time (such as about 4~6 hours) and filtered. Preferably, the obtained filter cake is slurried with a suitable organic solvent (such as EtOAc) at a suitable temperature (such as about 0~5° C.) for a suitable period of time (such as about 4~6 hours), and then filtered to provide the compound of Formula I. Before slurry, the filter cake can be washed with a suitable organic solvent (such as EtOAc). The volume ratio of the organic solvent used for slurry to the compound of Formula II used in the initial reaction is usually 1~5, such as 2~3. After filtered again, the filter cake can be washed with a suitable organic solvent (such as EtOAc).

The filter cake is dried under vacuum at a suitable temperature (such as about 45~50° C.) for a suitable period of time (such as about 16~20 hours) to provide the compound of Formula I. It should be understood that the amount of the organic solvent used for washing the filter cake can be easily determined according to actual situation.

In certain embodiments, the obtained compound of Formula I can, be further purified by recrystallization. For example, the compound of Formula I can be dissolved in an appropriate amount of a suitable organic solvent (such as DMSO). Generally, the amount of the organic solvent can be up to 10 times volume of the compound of Formula I. When dissolved, it can be stirred at a suitable temperature (such as about 15~25° C.) for a suitable period of time, such as about 2~4 hours. Then an appropriate amount (for example, the volume ratio of pure water to the compound of Formula I is up to about 10) of pure water was added dropwise and slowly within a suitable time period (such as within about 2 hours). Stirring is continued at the above temperature for a suitable period of time (such as 8~10 hours), and then the mixture is filtered.

In certain specific embodiments, the solvent used for recrystallization is DMSO and water; pure water (the volume ratio of pure water to the compound of Formula I is 8) is added to a solution of the compound of Formula I in DMSO (the volume ratio of DMSO to the compound of Formula I is 8) at 15~25° C. slowly, and stirred at 15~25° C. for 8~10 hours.

In one preferred embodiment the compound of Formula I is dissolved in DMSO (the volume ratio of DMSO to, the compound of Formula I is 8), the mixture is stirred at 15~25° C. for 2~4 hours, then pure water (the volume ratio of pure water to the compound of Formula I is 8) is added dropwise within 2 hours, the mixture is stirred at 15~25° C. for 8~10 hours and filtered.

The obtained filter cake can be slurried again by using an appropriate amount of pure water (for example, the volume ratio of pure water to the compound of Formula I is about 10) at the above temperature for a suitable period of time (about 4~6 hours), and filtered; the filter cake is washed with pure water, dried under vacuum to provide the purified compound of Formula I. During purification, the slurry can be sampled and analyzed by HPLC for in-process control (IPC).

In one embodiment, the present disclosure provides a process for preparing a compound of Formula II, and the process comprises the step of hydrolyzing a compound of Formula III:

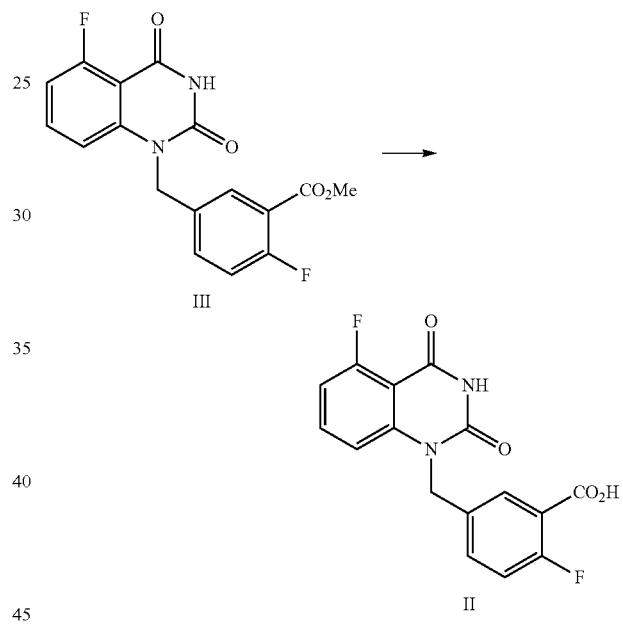

In the process for preparation, the compound of Formula III is added to a mixture of an aqueous inorganic base (such as KOH or NaOH) solution and an organic solvent (such as MeOH or EtOH). Generally, the mole ratio of the used inorganic base to the compound of Formula III is 1.5~2.0, and the volume ratio of the organic solvent to the compound of formula III is about 0.8~1.3, and the volume of water in the aqueous inorganic base solution is about 2.8~3.5 times volume of the compound of Formula III. The obtained mixed liquid can be stirred at a suitable temperature (such as about 40~50° C.) for a suitable period of time, such as about 16~30 hours, preferably 24~30 hours.

In certain embodiments, per 1 mol of the compound of Formula III is stirred in 1.8 mol of NaOH, 3 times volume of water (based on the volume of the compound of Formula III) and 1 time volume of MeOH (based on the volume of the compound of Formula III) at 40~50° C. for 24~30 hours.

Preferably, during the process of stirring, the mixture is sampled and analyzed by HPLC for IPC (IPC limit: III/II<1.0%, if III/II>1.0% stir another 4~8 hours or add another portion, of NaOH).

After the reaction is finished, the reaction liquid is cooled to a suitable temperature (such as 10~25° C.), an appropriate amount (for example, the volume ratio of water to the compound of Formula III is about 5.0~9.0) of water is added, an inorganic acid is added dropwise at the same temperature, the pH value of the reaction liquid is adjusted to 2~3 and then the mixture is stirred for a suitable period of time (such as about 1~2 hours). The inorganic acid can be hydrochloric acid, of which the concentration can be determined according to actual situation, as long as the pH value of the reaction liquid can be adjusted to the above range.

In certain embodiments, the reaction liquid is cooled to 10~25° C., water with 5.0~9.0 times volume of the compound of Formula III is added, the pH value is adjusted to 2~3 with 2N hydrochloric acid, and the mixture is continued to stir at the maintained temperature for 1~2 hours.

After stirring, the reaction liquid is filtered, and the filter cake is washed with water and dried under vacuum, usually dried under vacuum at 40~45° C. for 12~16 hours. Thus the compound of Formula II can be obtained.

In one embodiment, the present disclosure provides a process for preparing the compound of Formula III, and the process comprises the steps of reacting a compound of Formula IV with a compound of Formula V:

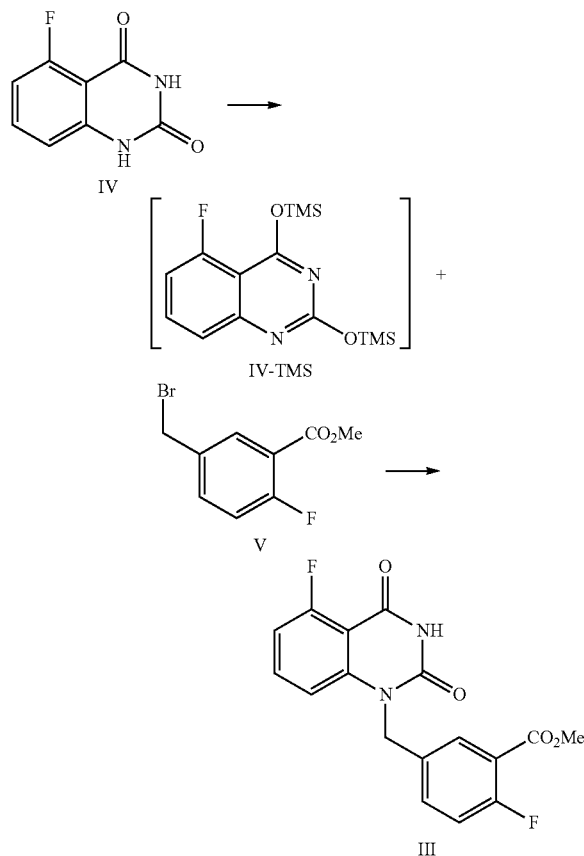

In the preparation process, firstly the compound of Formula IV is dissolved in a suitable solvent (such as toluene), hexamethyldisilazane (HMDS) is added, and then sulfuric acid is added dropwise. The mixed liquid is stirred at a suitable temperature (such as about 105~120° C., such as 108~112° C.) for a suitable period of time (such as about 40~60 hours) until all solids are dissolved completely. Under the protection of nitrogen, the reaction liquid is concentrated after cooled to a suitable temperature (such as about 55~65° C.), and then the obtained solid is cooled to a suitable temperature (such as 15~30° C.) under a nitrogen atmosphere to provide the intermediate IV-TMS, which is used directly for the next step reaction.

Usually, the amount of solvent is 7~9 times volume of the compound of Formula IV. For 1 mol of the compound of Formula IV, 2.0~3.0 mol of HMDS is used, and 0.04~0.06 mol of sulfuric acid is added dropwise.

The reaction of the intermediate of Formula IV-TMS with the compound of Formula V should be controlled to be anhydrous. The above obtained intermediate solid IV-TMS and the compound of Formula V are refluxed in an appropriate amount (for example, the volume ratio of the compound of Formula V to the compound of Formula IV-TMS is 1~3) of the first solvent (such as NMP or DMF) until the reaction is complete, usually stirred at 105~115° C. for 12~18 hours. During the period, the mixture preferably is sampled and analyzed by HPLC for IPC (IPC limit: IV/III<10%, if IV/III>10% stir another 2~4 hours). Preferably, for 1 mol of the compound of Formula IV-TMS, the amount of the compound of Formula V is 1.0~1.3 mol.

Then the second solvent (such as dioxane) is added to the reaction liquid slowly. After the reaction liquid is cooled to a suitable temperature (such as 65~75° C.), the third solvent (such as alcoholic solvent like MeOH and/or EtOH) is added dropwise slowly. Then the mixture is continued to stir at a suitable temperature (such as 65~75° C.) for about 0.5~1 hour. The volume ratio of the second solvent to the compound of Formula IV-TMS is usually 1.0~1.5. The volume ratio of the third solvent to the compound of Formula IV-TMS is usually 2.5~3.5.

After the reaction is finished, the reaction liquid is cooled to a suitable temperature (such as 0~5° C.), and maintained at this temperature and stirred for a suitable period of time (such as 1~2 hours). The mixture is filtered, and the filter cake is washed with MeOH and water, and dried under vacuum at 40~45° C. to provide the compound of Formula III.

In one embodiment of the above preparation process, the intermediate solid IV-TMS is refluxed with the compound of Formula V in DMF (the volume ratio of DMF to the compound of Formula IV-TMS is 1); then the second and third solvents are added, which are, dioxane and MeOH, respectively; after the reaction is finished, the reaction liquid is cooled to 0~5° C.

In one embodiment, the present disclosure provides a process for preparing the compound of Formula IV, and the process comprises a step of reacting a compound of Formula B with cyanate:

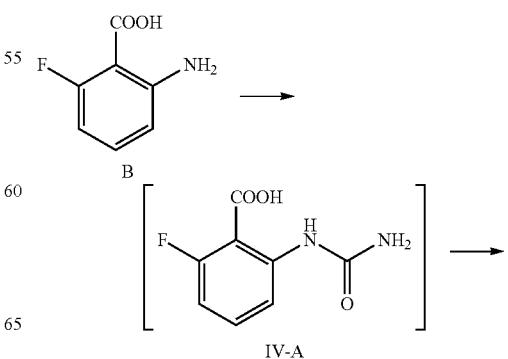

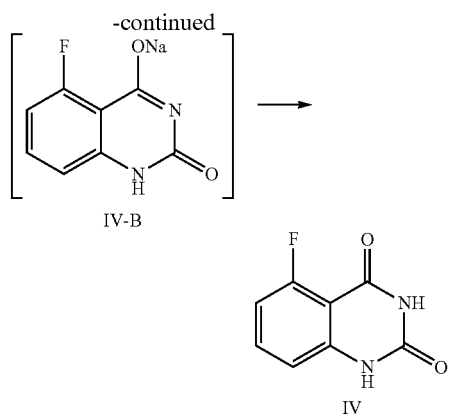

In the preparation process, the compound of Formula B is added to water, and then acetic acid is added, and the obtained mixed liquid is stirred at 5~15° C. for 20~30 min. In general, the compound of Formula B is added to water, wherein the volume ratio of water to the compound of Formula B is 30~40, and then acetic acid (the volume ratio of acetic acid to the compound of Formula B is 1.0~1.5) is added. After stirring, an aqueous cyanate solution (an appropriate amount of cyanate is dissolved in an appropriate amount of water, for example, for 1 mol of the compound of Formula B, 1.0~1.5 mol of cyanate is used, which is dissolved in water, wherein the volume ratio of water to the compound of Formula B is 2.0~3.0) is added dropwise to the mixed liquid at the temperature and the reaction liquid is stirred at 5~15° C. until the reaction is complete, usually for 1 hour. In general, cyanate is KOCN. For 1 mol of the compound of Formula B, 1.0~1.5 mol of cyanate is used. Preferably, the reaction liquid is sampled and analyzed by HPLC for IPC (IPC limit: B/IV-A<2%, if B/IV-A>2%, stir another 1~2 hours until the limit is reached).

In one preferred embodiment, for 1 mol of the compound of Formula B, the used aqueous cyanate solution is 1.2 mol of KOCN dissolved in water, wherein the volume ratio of water to the compound of Formula B is 2.5; the mixed liquid of the compound of Formula B, acetic acid and water is formulated by using 1.2 mol of acetic acid and water (wherein the volume ratio of water to the compound of Formula B is 35) per 1 mol of the compound of Formula B.

After the reaction is complete, an aqueous inorganic base solution (such as aqueous solution of KOH or NaOH) is added dropwise at a suitable temperature (such as below 0° C.), and the mixture is stirred at 10~25° C. until the reaction is complete, for example stirred for 16~20 hours. For 1 mol of the compound of Formula B, the said aqueous inorganic base solution can be prepared by dissolving 7~8 mol of inorganic base in water, wherein the volume ratio of water to the compound of Formula B is 2~4. Preferably, in the process of reaction, the reaction liquid is sampled and analyzed by HPLC for IPC (IPC limit: IV-A/IV-B<2%, if IV-A/IV-B>2%, stir another 4~8 hours).

Later, the reaction liquid is cooled to 0~5° C. and stirred for another 2~4 hours. Preferably, the reaction liquid is sampled and analyzed by HPLC for IPC (IPC limit: residual of the target compound IV in mother liquid, should be <0.5%, if IV>0.5%, stir another 1~2 hours). After the reaction is finished, the mixture is filtered, and the filter cake is washed with 0~5° C. water (1~3 times volume of the compound of Formula B).

The above filter cake can be put in another reaction kettle, water with the volume ratio of 25~35 to the compound of Formula B is added, the temperature is increased to 85~95° C., and the mixture is maintained at the temperature and stirred for 1.5~3 hours. The pH value of the reaction liquid is adjusted to 5~6 with an acid (for example 2.8~3.3 mol of the acid is used for 1 mol of the compound of Formula B), and the mixture is stirred at 85~95° C. for another 1~3 hours. The acid can be any conventional acid, preferably acetic acid. Then the reaction liquid is cooled to 0~5° C. and stirred for 2~4 hours. The reaction liquid is sampled and analyzed by HPLC for IPC (IPC limit: residual of the target compound IV in mother liquid<0.5%, if IV>0.5%, stir another 1~2 hours). After the reaction is finished, the mixture is filtered and the filter cake is washed with water (for example the volume is 3~5 times volume of the compound of Formula B). At last the solid is dried under vacuum at 45~50° C. for 14~20 hours to provide the compound of Formula IV.

As used herein and unless otherwise indicated, the term "process(es) of preparing" or "process(es) for the preparation" refers to the methods disclosed herein which are useful for preparing a compound disclosed herein. Modifications to the methods disclosed herein (e.g., compounds, starting materials, reagents, solvents, temperatures, reaction times, purification) are also encompassed by the methods and processes provided herein.

In the present disclosure, inorganic acids include all kinds of conventional inorganic acids in the field, such as hydrochloric acid, sulfuric acid, nitric acid, phosphoric acid, carbonic acid, acetic acid, hydrofluoric acid, etc. A mixture of one or more inorganic acids can be used.

In the present disclosure, solvents can be all kinds of conventional used solvents in the field, including organic solvents and water. The organic solvents include but not limited to DMSO, ethyl acetate, n-heptane, methyl tert-butyl ether, alcoholic solvent, toluene, N-methyl pyrrolidone, N,N-dimethyl formamide, dichloromethane, isopropyl acetate and acetonitrile, etc. Alcoholic solvents include MeOH and EtOH etc. A mixture of one or more solvents can be used.

As used herein and unless otherwise indicated, the term "adding", "reacting" or "in the presence of" and the like means contacting one reactant, reagent, solvent, catalyst, reactive group or the like with another reactant, reagent, solvent, catalyst, reactive group or the like. Reactants, reagents, solvents, catalysts, reactive groups or the like can be added individually, simultaneously or separately and can be added in any order, unless otherwise specified. They can be added in the presence or absence of heat and can optionally be added under an inert atmosphere. "Reacting" can refer to in situ formation or intramolecular reaction where the reactive groups are in the same molecule.

In the present disclosure, "filter cake" refers to the obtained precipitate. The term does not have any restrictions on the shape of the precipitate.

The following examples are illustrative, but not limiting of the method and preparations of the present disclosure. Other suitable modifications and adaptations of the variety of conditions and parameters normally encountered in reaction and which are obvious to those skilled in the art are within the spirit and scope of the disclosure.

EXAMPLES

General Remarks

The following examples further illustrate the embodiments described herein, which shall, not be interpreted as the

Example 1

Preparation of 5-fluoroquinazoline-2,4(1H,3H)-dione, compound of Formula IV

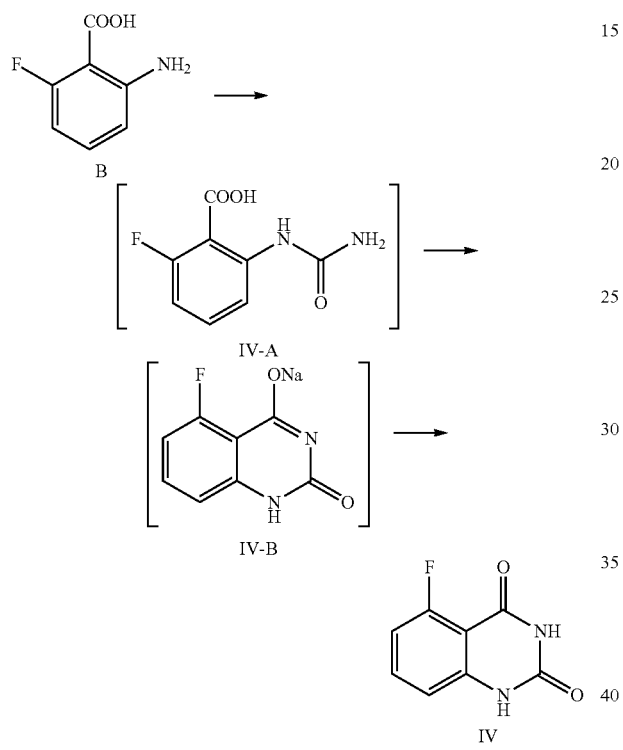

In a reaction kettle, to 2-amino-6-fluorobenzoic acid (B, 6.0 Kg, 38.68 mol) was added water (35 times volume of the compound of Formula B), then acetic acid (46.42 mol) was added, and the mixture was stirred at 5~15° C. for 20~30 min. At the maintained temperature of 5~15° C., the solution of KOCN (46.42 mol) dissolved in water (2.5 times volume of the compound of Formula B) was added to the above mixed liquid dropwise, and the mixture was stirred at 5~15° C. for 1 hour, which was sampled and analyzed by HPLC for IPC (IPC limit: B/IV-A<2%, if B/IV-A>2% stir another 1~2 hour until the limit was reached) and found to meet the limit (B/IV-A=0.7%). After the reaction was complete, 3N aqueous NaOH solution (NaOH (299.77 mol) dissolved in water (3 times volume of the compound of Formula B)) was added to the reaction mixture dropwise at a temperature below 0° C., and stirred at 10~25° C. for another 16~20 hours. The mixture was sampled and analyzed by HPLC for IPC (IPC limit IV-A/IV-B<2%, if IV-A/IV-B>2% stir another 4~8 hours) and found to meet the limit (IV-A/IV-B=0.3%). After the reaction was complete, the reaction liquid was cooled to 0~5° C. and stirred for another 2~4 hours, which was sampled and analyzed by HPLC for IPC (IPC limit: residual of the target compound IV in mother liquid<0.5%, if IV>0.5% stir another 1~2 hours). After the reaction was finished, the mixture was filtered and the filter cake was washed with 0~5° C. water (1~3 times volume of the compound of Formula B). The obtained filter cake was put in another reaction kettle, to which water (the volume ratio of water to the compound of Formula B was 30) was added, the mixture was heated to 85~95° C., and maintained at the temperature and stirred for 2 hours. The pH value of the reaction liquid was adjusted to 5~6 with acetic acid (119.91 mol), and the mixture was maintained at the temperature of 85~95° C. and stirred for 2 hours. Then the reaction liquid was cooled to 0~5° C. and stirred for 2~4 hours, which was sampled and analyzed, by HPLC for IPC (residual, of the target compound IV in mother liquid<0.5%, if IV>0.5% stir another 1~2 hours). After the reaction was finished, the mixture was filtered and the filter cake was washed with water (5 times volume of the compound of Formula B) and dried under vacuum at 45~50° C. for 16 hours to provide 6.1 Kg of the target compound 5-fluoroquinazoline-2,4(1H,3H)-dione (IV, HPLC, purity: 98.9%, yield: 86.9%) as an off-white solid. HPLC (std): 6.28 min; $^1$H NMR (400 MHz, DMSO-$d_6$): δ 11.25 (s, 2H), 7.59 (dd, J=13.8, 8 Hz, 1H), 6.96 (d, J=8 Hz, 1H), 6.91 (dd, J=11.4, 8.4 Hz, 1H); KF: 0.4%.

Example 2

Preparation of 5-fluoro-1-(4-fluoro-3-methoxycarbonylbenzyl)quinazoline-2,4(1H,3H)-dione, Compound of Formula III

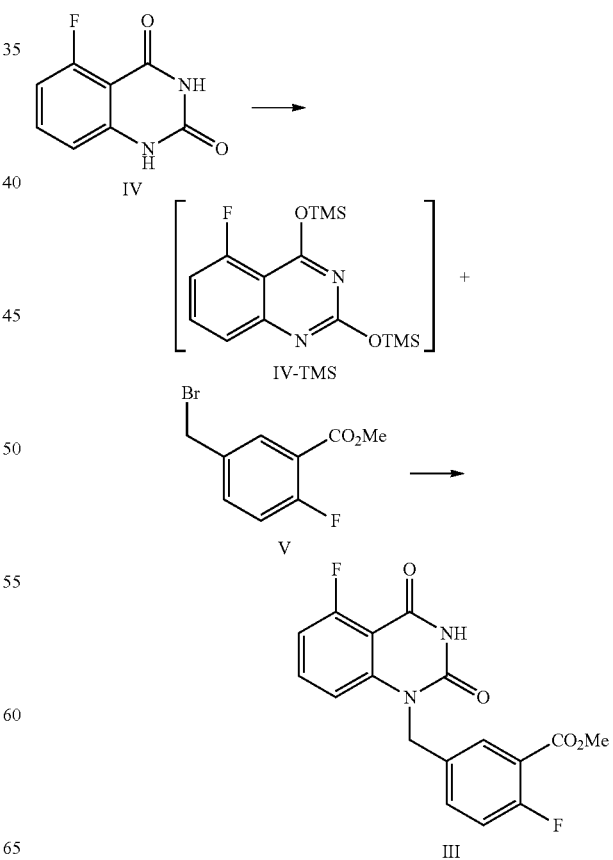

In a reaction kettle, to 5-fluoroquinazoline-2,4(1H,3H)-dione (IV, 4.4 Kg, 24.43 mol) was added toluene (8 times volume of the compound of Formula IV) and then hexamethyldisilazane (HMDS, 61.08 mol). Then sulfuric acid (1.22 mol) was added dropwise. The mixed liquid was heated to 108~112° C. for refluxing and stirred for 48 hours until all solids were dissolved. Under nitrogen protection, the reaction liquid was cooled to 55~65° C. and concentrated, and then the solid was cooled to 15~30° C. in nitrogen atmosphere to provide the target compound 5-fluoro-2,4-di(trimethylsilyloxy)quinazoline IV-TMS as a crude product used for the next step reaction directly.

To 5-fluoro-2,4-di(trimethylsilyloxy)quinazoline IV-TMS was added methyl 5-bromomethyl-2-fluorobenzoate (V, 26.87 mol) and the solvent N,N-dimethylformamide (DMF, 1 time volume of the compound of Formula IV-TMS). The mixture was heated to 105~115° C. and stirred for 16 hours, which was sampled and analyzed by HPLC for IPC (IPC limit: IV/III<10%, if IV/III>10%, stir another 2~4 hours).

After the reaction was complete, dioxane with a volume ratio of 1.2 to the compound of Formula IV-TMS was added to the reaction liquid slowly. After the reaction liquid was cooled to 65~70° C., MeOH with volume ratio of 3 to the compound of Formula IV-TMS was added dropwise slowly. Then the mixture was stirred at 65~70° C. for 0.5~1 hour. After the reaction was finished, the reaction liquid was cooled to 0~5° C. and maintained at the above temperature and stirred for 1~2 hours, and then filtered. The filter cake was washed with MeOH (2 times volume of the compound of Formula IV-TMS) and water (4 times volume of the compound of Formula IV-TMS). The filter cake was dried under vacuum at 40~45° C. to provide 6.9 Kg of the target compound 5-fluoro-1-(4-fluoro-3-methoxycarbonylbenzyl)quinazoline-2,4(1H,3H)-dione (III, yield: 74.6%) as a white solid. HPLC (std): 8.49 min; KF: 0.21%; Residue on ignition: 0.02%; GC (residual solvent): MeOH 0.06%; Dioxane 0.07%; N,N-Dimethylformamide 0.37%.

Example 3

Preparation of 5-fluoro-1-(4-fluoro-3-carboxybenzyl)quinazoline-2,4(1H,3H)-dione, compound of Formula II

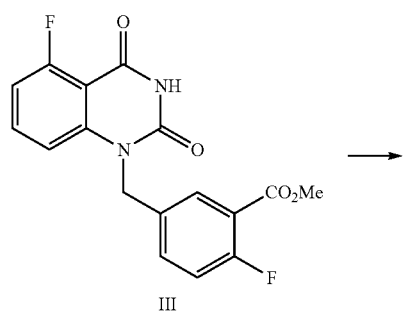

III

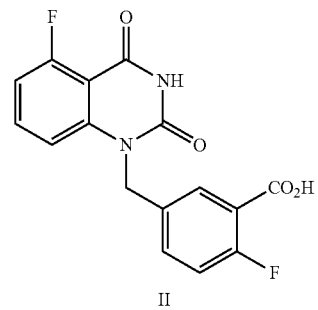

II

In a reaction kettle, NaOH (11.75 mol) was added to water (3 times volume of the compound of Formula III) and stirred until all solids were dissolved. Then MeOH (1 time volume of the compound of Formula III) and 5-fluoro-1-(4-fluoro-3-methoxycarbonylbenzyl)quinazoline-2,4(1H,3H)-dione (III, 2.26 Kg, 6.53 mol) were added. The mixed liquid was heated to 40~50° C. and maintained at this temperature and stirred for 24~30 hours, which was sampled and analyzed by HPLC for IPC (IPC limit: III/II<1.0%, if III/II>1.0%, stir another 4~8 hours or add another portion of NaOH). After the reaction was finished, the reaction liquid was cooled to 10~25° C., to which water (5.0~9.0 times volume of the compound of Formula III) was added, and 2N hydrochloric acid (the mole ratio of hydrochloric acid to the compound of Formula III was 0.9~3) was added dropwise at 10~25° C. to adjust the pH value to 2~3, and the mixture was maintained at the temperature and stirred for 1~2 hours. The mixture was filtered and the filter cake was washed with water (3 times volume of the compound of Formula III×2). The filter cake was dried under vacuum at 40~45° C. for 12~16 hours to provide 2.01 Kg of the target compound 5-fluoro-1-(4-fluoro-3-carboxybenzyl)quinazoline-2,4(1H,3H)-dione (II, yield: 96.0%) as a white solid. HPLC (std): 7.44 min; $^1$H NMR (400 MHz, DMSO-$d_6$): δ 13.30 (brs, 1H), 11.71 (s, 1H), 7.83 (dd, J=11.4, 8.4 Hz, 1H), 7.66-7.61 (m, 1H), 7.58-7.54 (m, 1H), 7.27 (dd, J=10.6, 8.6 Hz, 1H), 7.09 (d, J=8.8 Hz, 1H), 706 (dd, J=11, 8.2 Hz, 1H), 5.31 (s, 2H); KF: 0.5%; GC (residual solvent): MeOH 0.4%.

Example 4

Preparation of 5-fluoro-1-(4-fluoro-3-(4-(pyrimidin-2-yl)piperazine-1-carbonyl)benzyl)quinazoline-2,4(1H,3H)-dione, compound of Formula I

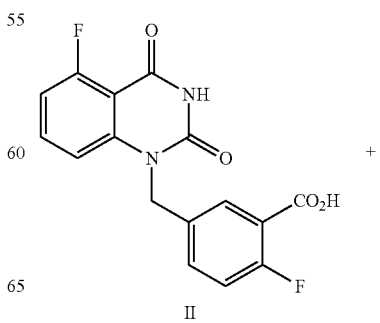

II

-continued

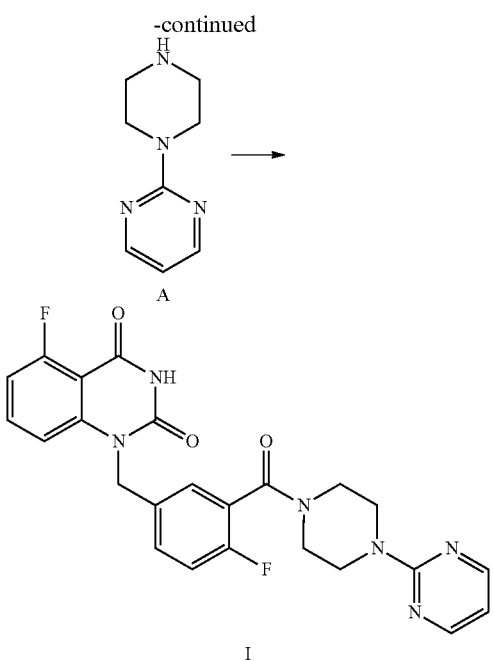

Synthesis: In a reaction kettle, to 5-fluoro-1-(4-fluoro-3-carboxybenzyl)quinazoline-2,4(1H,3H)-dione (II, 1.8 Kg, 5.42 mol) was added EtOAc (20 times volume of the compound of Formula II), followed by propyl phosphoric acid anhydride ($T_3P$, 8.67 mol, 50% EtOAc solution) and N-di(isopropyl)ethylamine (DIPEA, 17.34 mol). The reaction liquid was heated to 65~75° C. and maintained at the temperature and stirred for 10~20 min, then a solution of 2-(piperazin-1-yl)pyrimidine (A, 5.96 mol) dissolved in EtOAc (2.5 times volume of the compound of Formula II) was added at 73~80° C., and the mixture was stirred at 70~80° C. for 12~16 hours. After the reaction was finished, the reaction liquid was cooled to 0~5° C. and stirred for 4~6 hours, filtered, and the filter cake was washed with EtOAc (2~3 times volume of the compound of Formula II). The cake was slurried with EtOAc (2~3 times volume of the compound of Formula II) at 0~5° C. for 4~6 hours, filtered, and the filter cake was washed with EtOAc (2~3 times volume of the compound of Formula II). The product was dried under vacuum at 45~50° C. for 16~20 hours to provide 2.48 Kg of the target compound 5-fluoro-1-(4-fluoro-3-(4-(pyrimidin-2-yl)piperazine-1-carbonyl)benzyl)quinazoline-2,4(1H,3H)-dione (I, yield: 89.4%) as a white powder. HPLC (std): 7.76 min; $^1$H NMR (400 MHz, DMSO-$d_6$): δ 11.68 (brs, 1H), 8.40-8.38 (m, 2H), 7.67-7.61 (m, 1H), 7.48-7.44 (m, 1H), 7.41 (dd, J=6.4, 2 Hz, 1H), 7.30 (t, J=9 Hz, 1H), 7.06-7.01 (m, 2H), 6.68 (t, J=4.6 Hz, 1H), 5.31 (s, 2H), 3.83-3.81 (m, 2H), 3.70-3.64 (m, 4H), 3.24-3.22 (m, 2H); KF: 2.4%.

Purification:

In a reaction kettle, dimethylsulfoxide (DMSO, 8 times volume of the compound of Formula I) was added to 5-fluoro-1-(4-fluoro-3-(4-(pyrimidin-2-yl)piperazine-1-carbonyl)benzyl)quinazoline-2,4(1H,3H)-dione (I, 2.48 Kg, 5.18 mol), and the mixture was stirred at 15~25° C. for 2~4 hours. Then water of 8 times volume of the compound of Formula I was added dropwise slowly within 2 hours. The mixture was stirred at 15~25° C. for 8~10 hours, which was sampled and analyzed by HPLC for IPC (IPC, the purity of the target compound was 98.6%). The mixture was filtered and the filter cake was slurried with pure water (10 times volume of the compound of Formula I) at 15~25° C. for 4~6 hours, then filtered and the filter cake was washed with pure water (2~3 times volume of the compound of Formula I). The filter cake was dried under vacuum at 45~50° C. for 16~20 hours to provide 2.02 Kg of the target compound 5-fluoro-1-(4-fluoro-3-(4-(pyrimidin-2-yl)piperazine-1-carbonyl)benzyl)quinazoline-2,4(1H,3H)-dione (I, yield: 88.4%) as an off-white crystalline powder. Mp=278.88° C.; HPLC (std): 12.57 min; $^1$H NMR (400 MHz, DMSO-$d_6$): δ 11.69 (s, 1H), 8.39-8.38 (m, 2H), 7.67-7.61 (m, 1H), 7.48-7.44 (m, 1H), 7.42 (dd, J=6, 2 Hz, 1H), 7.30 (t, J=10 Hz, 1H), 7.06-7.01 (m, 2H), 6.67 (t, J=5 Hz, 1H), 5.31 (s, 2H), 3.83-3.80 (m, 2H), 3.69-3.63 (m, 4H), 3.25-3.22 (m, 2H); KF: 5.5%; Residue on ignition: 0.03%; GC (residual solvent): DMSO 1025 ppm; MeOH<100 ppm; EtOAc 343 ppm; N,N-Diisopropylethylamine<100 ppm; Toluene<100 ppm; N,N-Dimethylformamide<200 ppm; Dioxane<100 ppm.

Having now fully described this disclosure, it will be understood by those of ordinary skill in the art that the same can be performed within a wide and equivalent range of conditions, formulations and other parameters without affecting the scope of the disclosure or any embodiment thereof. All patents, patent applications and publications cited herein are fully incorporated by reference herein in their entirety.

What is claimed is:

1. A method for preparing a compound of Formula I:

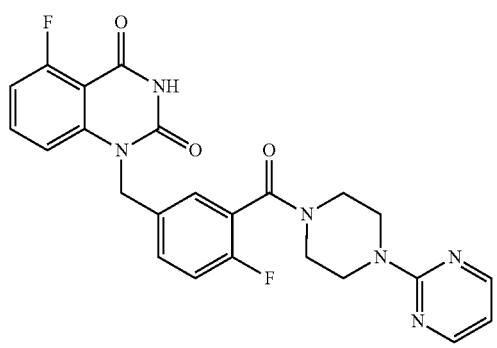

wherein the method comprises condensing at 70~80° C. with stirring, a compound of Formula II with a compound of Formula A, in the presence of a condensation agent, an organic base, and an organic solvent:

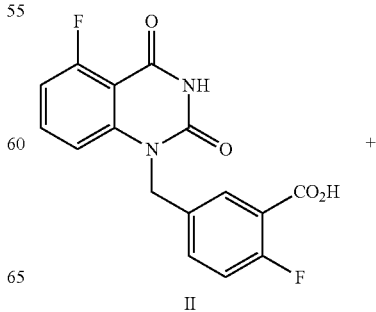

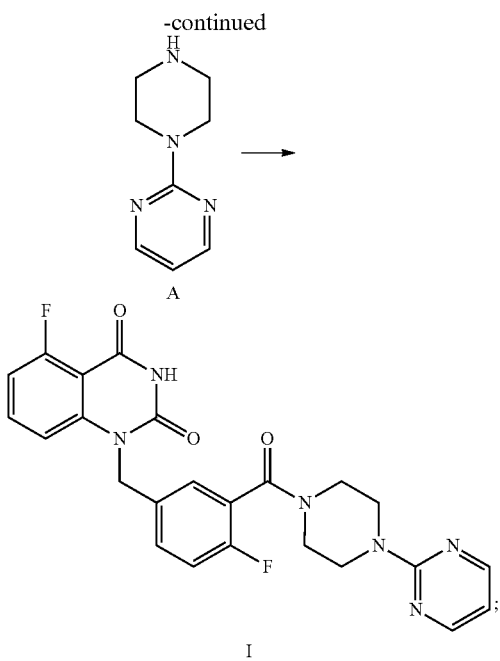

and after completion of stirring at 70~80° C., cooling the reaction liquid to 0~5° C., stirring, and filtering to provide the compound of Formula I.

2. The method of claim 1, wherein the method comprises one or more of the following features:
the condensation agent is 2-(7-aza-1H-benzotriazole-1-yl)-N,N,N',N'-tetramethyluronium hexafluorophosphate, O-(benzotriazol-1-yl)-N,N,N',N'-tetramethyluronium tetrafluoroborate, O-benzotriazole-N,N,N',N'-tetramethyl-uronium-hexafluorophosphate or propyl phosphoric acid anhydride, or any mixture thereof;
the organic base is N-methylmorpholine, DIPEA, or any mixture thereof; and
the organic solvent is EtOAc.

3. The method of claim 1, wherein the method comprises one or more of the following features:
for 1 mol of the compound of Formula II, 1.3~2.0 mol of the condensation agent is used;
for 1 mol of the compound of Formula II, 2.8~3.5 mol of the organic base is used;
the volume of the used organic solvent is 15~30 times volume of the compound of Formula II; and
for 1 mol of the compound of Formula II, 1.0~1.3 mol of the compound of Formula A is used.

4. The method of claim 1, wherein
the compound of Formula II, the organic solvent, the condensation agent, and the organic base are stirred at 65~75° C. until all solids are dissolved, then the compound of Formula A is added; and
after the completion of stirring at 70~80° C. and cooling the reaction liquid to 0~5° C., the reaction liquid is stirred for 4~6 hours, and filtered to provide the compound of Formula I.

5. The method of claim 1, wherein the method further comprises recrystallizing in the presence of a solvent of the reaction product obtained from the condensation reaction, in order to provide a purified compound of Formula I.

6. The method of claim 5, wherein the reaction product I-obtained from the condensation reaction is dissolved in DMSO, with a volume ratio of DMSO to the reaction product not greater than 10, and the mixture is stirred at 15~25° C. for 2~4 hours; then pure water, with a volume ratio of water to the reaction product not greater than 10, is added dropwise within 2 hours, and the mixture is stirred at 15~25° C. for 8~10 hours and filtered.

7. The method of claim 6, wherein after stirring with water and filtering, the obtained filter cake is slurried with pure water again, with a volume ratio of pure water to the reaction product not greater than 10, at 15~25° C. for 4~6 hours, filtered, and the filter cake is washed with pure water and dried under vacuum to provide a purified compound of Formula I.

8. The method of claim 1, wherein the compound of Formula II is prepared by a method comprising the following reaction:

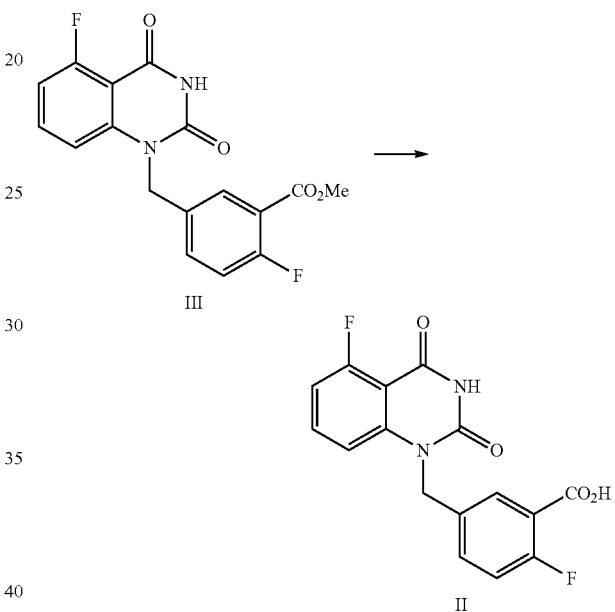

hydrolyzing in a solvent, the compound of Formula III in the presence of an inorganic base, then adjusting the pH value of the reaction liquid to 2~3 to provide the compound of Formula II.

9. The method of claim 8, wherein the method comprises one or more of the following features:
the solvent is an alcoholic solvent and/or water;
the solvent is an alcoholic solvent, wherein the amount of the alcoholic solvent is 0.8~1.3 times volume of the compound of Formula III;
the inorganic base is an aqueous solution of KOH and/or NaOH;
for 1 mol of the compound of Formula III, 1.5~2.0 mol of the inorganic base is used;
a mixture of the compound of Formula III, an organic solvent and an aqueous inorganic base solution is stirred at 40~50° C. for 16~30 hours, allowing for a hydrolysis reaction; and
after the hydrolysis reaction is finished, the reaction liquid is cooled to 10~25° C., to which water is added, and an inorganic acid is added dropwise to adjust the pH value of the reaction liquid to 2~3; the mixture is stirred for 1~2 hours, and then filtered to provide the compound of Formula II.

10. The method of claim 8, wherein the compound of Formula III is prepared by a method comprising the following reactions:

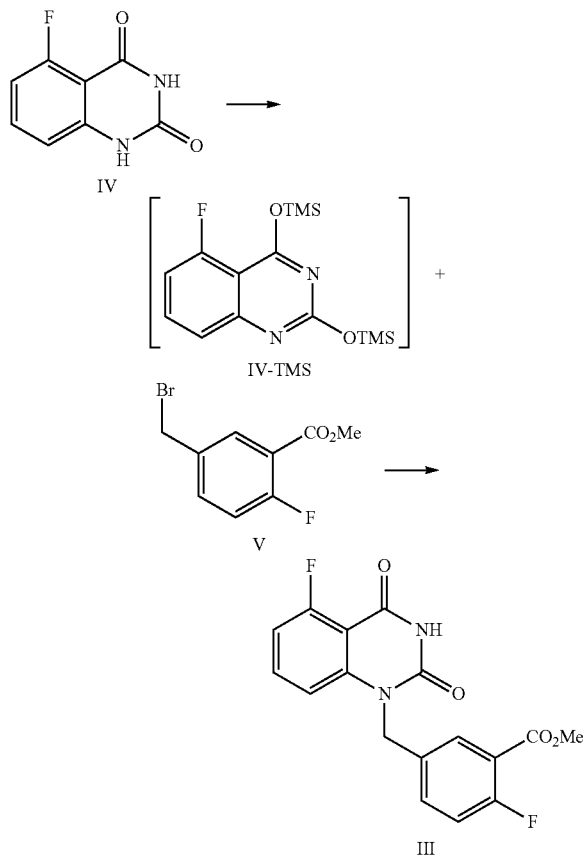

1) refluxing in an organic solvent, the compound of Formula IV with hexamethyldisilazane in the presence of an inorganic acid to provide the intermediate of Formula IV-TMS; and
2) reacting under anhydrous conditions, the intermediate of Formula IV-TMS with the compound of Formula V in an organic solvent under reflux conditions to provide the compound of Formula III.

11. The method of claim 10, wherein 1) comprises one or more of the following features:
the organic solvent is toluene;
the inorganic acid is sulfuric acid;
the amount of the organic solvent is 7~9 times volume of the compound of Formula IV;
for 1 mol of the compound of Formula IV, 2.0~3.0 mol of hexamethyldisilazane is used;
for 1 mol of the compound of Formula IV, 0.04~0.06 mol of the inorganic acid is used;
the reflux conditions comprise stirring at 105~120° C. until all solids are dissolved completely; and
after refluxing, the reaction liquid is cooled to 55~65° C. in an inert atmosphere, then concentrated, and the obtained concentrated solution is cooled to 15~30° C. in an inert atmosphere to provide the intermediate of Formula IV-TMS.

12. The method of claim 10, wherein 2) comprises one or more of the following features:
the organic solvent is N-methyl-2-pyrrolidone and/or N,N-dimethylformamide;
the reflux conditions comprise stirring at 105~115° C. for 12~18 hours;
for 1 mol of the intermediate of Formula IV-TMS, 1.0~1.3 mol of the compound of Formula V is used; and
after the refluxing is finished, dioxane is added to the reaction liquid, which is cooled to 65~75° C., then alcoholic solvent is added, and the mixture is stirred at 65~75° C. for about 0.5~1 hour; the reaction liquid is cooled to 0~5° C., stirred for 1~2 hours, and filtered to provide the compound of Formula III.

13. The method of claim 12, wherein
the alcoholic solvent is MeOH and/or EtOH, the amount of the alcoholic solvent is 2.5~3.5 times volume of the intermediate of Formula IV-TMS; and/or
the amount of dioxane is 1.0~1.5 times volume of the intermediate of Formula IV-TMS.

14. The method of claim 10, wherein the compound of Formula IV is prepared from a compound of Formula B by a method comprising the following reactions:

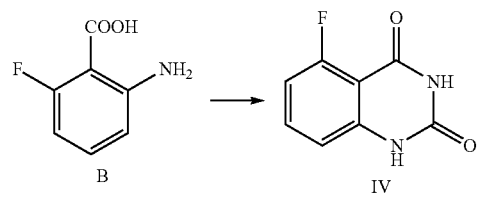

1) reacting a compound of Formula B first with an aqueous cyanate solution, then with an aqueous inorganic base solution; and
2) adjusting the pH value of the aqueous solution of the product in 1) to 5~6 to provide the compound of Formula IV.

15. The method of claim 14, wherein 1) comprises one or more of the following features:
the cyanate is KOCN;
for 1 mol of the compound of Formula B, 1.0~1.5 mol of cyanate is used, and the aqueous cyanate solution is obtained by dissolving 1.0~1.5 mol of cyanate in water, wherein the volume ratio of water to the compound of Formula B is 2.0~3.0;
the compound of Formula B is added first to water, then acetic acid is added, and the mixture is stirred at 5~15° C.;
for 1 mol of the compound of Formula B, 1.0~1.5 mol of acetic acid is used, and the volume ratio of water to the compound of Formula B is 30~40;
the aqueous cyanate solution is added dropwise to a mixed liquid of the compound of Formula B, acetic acid and water, and the mixture is stirred until the reaction is complete;
the aqueous inorganic base solution is an aqueous solution of KOH and/or NaOH;
for 1 mol of the compound of Formula B, the amount of the inorganic base is 7~8 mol, and the aqueous inorganic base solution is prepared by dissolving the inorganic base in water, wherein the volume ratio of water to the compound of Formula B is 2~4; and
the aqueous inorganic base solution is added below 0° C., then the mixture is stirred at 10~25° C. until the reaction is complete.

16. The method of claim 15, wherein in 1), after the aqueous inorganic base solution is added below 0° C., the mixture is stirred at 10~25° C. until the reaction is complete, and in 2), the reaction liquid obtained after adjusting the pH value is cooled to 0~5° C., stirred for 2~4 hours, and filtered.

17. The method of claim 14, wherein 2) comprises one or more of the following features:
the product obtained from 1) is added to water, and the mixture is heated to 85~95° C. and stirred at this temperature for 1.5~3 hours to provide an aqueous solution of the reaction product;
the product from 1) is dissolved in water, wherein the volume ratio of water to the compound of Formula B is 25~35; and
the pH value of the reaction liquid is adjusted to 5~6 with acetic acid, and the mixture is stirred at 85~95° C. for 1~3 hours, then the reaction liquid is cooled to 0~5° C., stirred for 2~4 hours, and filtered to provide the compound of Formula IV.

18. The method of claim 1, wherein
the organic solvent is EtOAc;
the condensation agent is propyl phosphoric acid anhydride;
the organic base is DIPEA;
for 1 mol of the compound of Formula II, 1.3~2.0 mol of the condensation agent is used;
for 1 mol of the compound of Formula II, 2.8~3.5 mol of the organic base is used;
the volume of the organic solvent is 15~25 times volume of the compound of Formula II; and
for 1 mol of the compound of Formula II, 1.0~1.3 mol of the compound of Formula A is used.

19. The method of claim 18, wherein
the compound of Formula II, the organic solvent, the condensation agent, and the organic base are stirred at 65~75° C. until all solids are dissolved, then the compound of Formula A is added, wherein the compound of Formula A is dissolved in the same organic solvent used to dissolve the compound of Formula II;
the resultant mixture of the compounds of Formula II and Formula A is stirred at 70~80° C. for 12~16 hours to allow for the condensation reaction;
after the completion of stirring at 70~80° C. and cooling the reaction liquid to 0~5° C., the reaction liquid is stirred for 4~6 hours, and filtered to provide the compound of Formula I; and
the obtained solid from filtration is slurried with the organic solvent at 0~5° C. and filtered again.

20. The method of claim 19, wherein, after the obtained solid from the filtration is slurried with the organic solvent at 0~5° C. and filtered again, the resultant product is subjected to recrystallization comprising dissolving the resultant product in DMSO, with a volume ratio of DMSO to the resultant product not greater than 10, stirring the resultant mixture at 15~25° C. for 2~4 hours; adding pure water, with a volume ratio of water to the resultant product not greater than 10, dropwise within 2 hours; stirring the resultant mixture at 15~25° C. for 8~10 hours and filtering; slurrying the obtained filter cake with pure water, with a volume ratio of pure water to the resultant product not greater than 10, at the above temperature for 4~6 hours again, filtering, and washing the filter cake with pure water and drying under vacuum to provide the purified compound of Formula I.

* * * * *